US009131592B2

(12) United States Patent (10) Patent No.: US 9,131,592 B2
Kojima et al. (45) Date of Patent: Sep. 8, 2015

(54) MOBILE X-RAY APPARATUS

(75) Inventors: Akira Kojima, Tokyo (JP); Tomokazu Takae, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 269 days.

(21) Appl. No.: 13/880,835

(22) PCT Filed: Nov. 17, 2011

(86) PCT No.: PCT/JP2011/076473
§ 371 (c)(1),
(2), (4) Date: Apr. 22, 2013

(87) PCT Pub. No.: WO2012/067171
PCT Pub. Date: May 24, 2012

(65) Prior Publication Data
US 2013/0223596 A1 Aug. 29, 2013

(30) Foreign Application Priority Data

Nov. 18, 2010 (JP) .................................. 2010-257820

(51) Int. Cl.
*H05G 1/10* (2006.01)
*H05G 1/12* (2006.01)
(Continued)

(52) U.S. Cl.
CPC ................ *H05G 1/12* (2013.01); *A61B 6/4405* (2013.01); *A61B 6/56* (2013.01); *H02J 9/061* (2013.01); *H05G 1/10* (2013.01)

(58) Field of Classification Search
CPC .......... A61B 6/4405; A61B 6/56; H05G 1/10; H05G 1/12; H02J 9/061

USPC ................................... 378/101–104, 197, 198
See application file for complete search history.

(56) References Cited

U.S. PATENT DOCUMENTS

| 4,797,907 A | 1/1989 | Anderton |
| 5,808,376 A | 9/1998 | Gordon et al. |
| 6,169,782 B1 * | 1/2001 | Zetterlund .................... 378/103 |

(Continued)

FOREIGN PATENT DOCUMENTS

| JP | A-5-276688 | 10/1993 |
| JP | A-2003-9424 | 1/2003 |

(Continued)

OTHER PUBLICATIONS

Apr. 17, 2014 Extended European Search Report issued in European Patent Application No. 11842266.6.

(Continued)

*Primary Examiner* — Allen C. Ho
(74) *Attorney, Agent, or Firm* — Oliff PLC

(57) ABSTRACT

A mobile X-ray apparatus that performs a stable operation even if a sudden voltage drop or momentary power interruption occurs during operation of a commercial AC power source. The mobile X-ray apparatus includes a plug for connection to a commercial AC power source, a battery charged from the commercial AC power source through the plug, a unit that operates by being supplied with electricity from the commercial AC power source connected through the plug, and a second circuit including a rectifier that supplies electricity to the unit from the battery if a voltage from the commercial AC power source falls to or below a regulated value while the unit is being operated by the electricity supply from the commercial AC power source.

8 Claims, 7 Drawing Sheets

(51) Int. Cl.
*A61B 6/00* (2006.01)
*H02J 9/06* (2006.01)

(56) References Cited

U.S. PATENT DOCUMENTS

| | | | | |
|---|---|---|---|---|
| 7,309,159 | B2 * | 12/2007 | Watanabe | 378/198 |
| 7,664,228 | B2 * | 2/2010 | Yi | 378/101 |
| 7,764,765 | B2 * | 7/2010 | Ohta et al. | 378/91 |
| 7,826,586 | B2 * | 11/2010 | Nakayama et al. | 378/15 |
| 7,974,381 | B2 * | 7/2011 | Anderton et al. | 378/102 |
| 8,385,504 | B2 * | 2/2013 | Hattrup et al. | 378/101 |
| 8,542,798 | B2 * | 9/2013 | Sung et al. | 378/103 |
| 8,546,777 | B2 * | 10/2013 | Utsunomiya | 250/580 |
| 8,552,595 | B2 * | 10/2013 | Bohori et al. | 307/104 |
| 8,705,699 | B2 * | 4/2014 | Fuse et al. | 378/102 |
| 9,060,741 | B2 * | 6/2015 | Fuse et al. | A61B 6/586 |

| | | | |
|---|---|---|---|
| 2005/0135560 | A1 | 6/2005 | Dafni et al. |
| 2006/0242552 | A1 | 10/2006 | Tanaka |
| 2007/0253540 | A1 | 11/2007 | Anderton et al. |

FOREIGN PATENT DOCUMENTS

| | | |
|---|---|---|
| JP | 2006-304886 | 11/2006 |
| JP | A-2010-46315 | 3/2010 |
| JP | A-2010-94327 | 4/2010 |
| WO | WO 2008/057713 A2 | 5/2008 |
| WO | WO 2010/100736 A1 | 9/2010 |
| WO | WO 2010/122906 A1 | 10/2010 |

OTHER PUBLICATIONS

Feb. 14, 2012 International Search Report issued in International Application No. PCT/JP2011/076473 (with translation).

* cited by examiner

FIG.3

| | FIRST SWITCH | SECOND SWITCH | KEY SWITCH (OPERATION FROM MODE SELECTOR 51) | COMMERCIAL AC POWER SOURCE AND PLUG |
|---|---|---|---|---|
| EXCLUSIVE CHARGING MODE | OFF | OFF | OFF | CONNECTION |
| CHARGING AND AC DRIVING MODE | ON | OFF | ON | CONNECTION |
| BATTERY DRIVING MODE (ALL FUNCTIONS) | ON | ON | ON | NON-CONNECTION |
| BATTERY DRIVING MODE (IMAGING CONTROL) | OFF | ON | ON | NON-CONNECTION |
| BATTERY DRIVING MODE (UNIT) | ON | OFF | ON | NON-CONNECTION |
| STOP MODE | OFF | OFF | OFF | NON-CONNECTION |

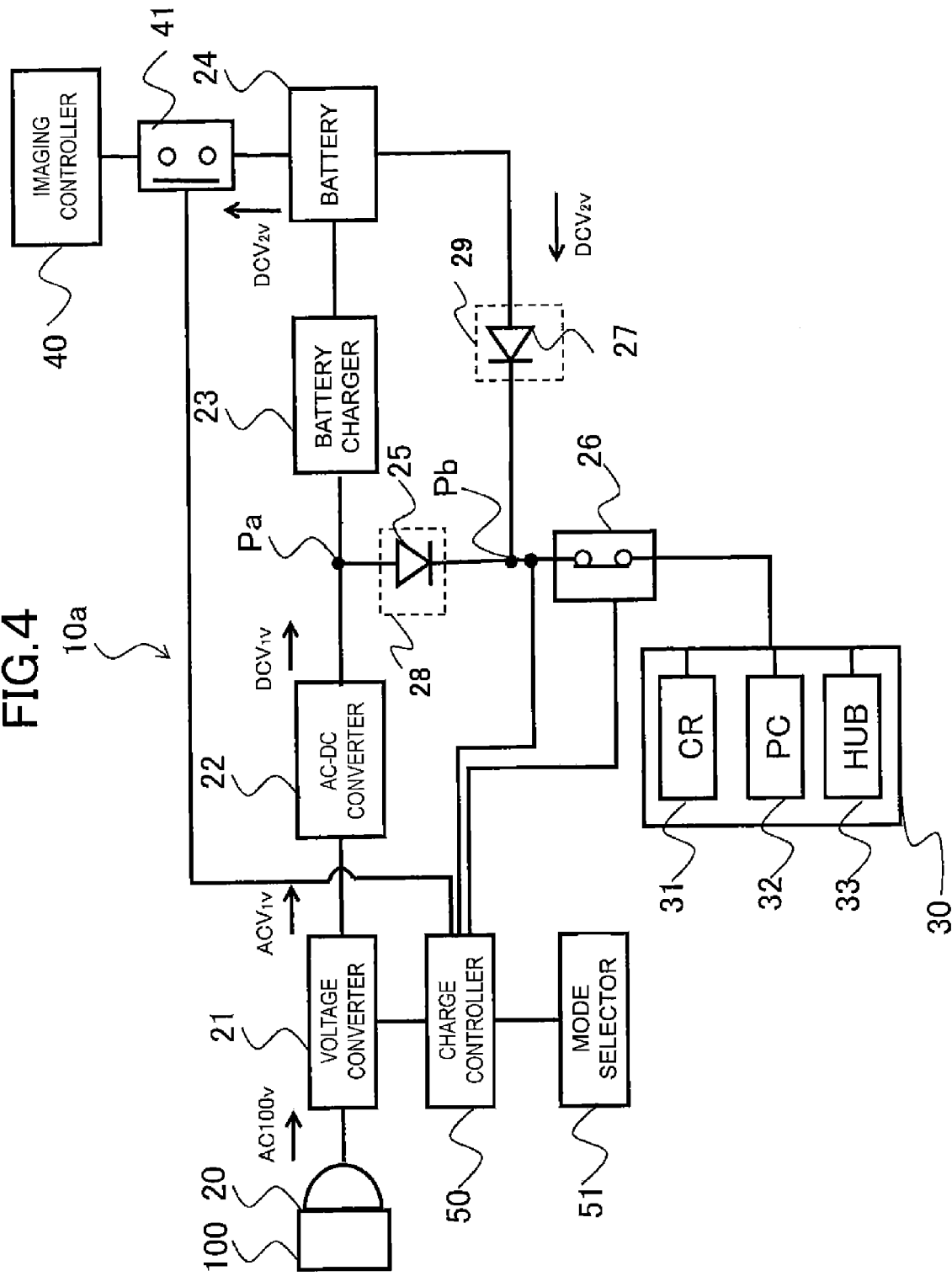

FIG.7

| | THIRD SWITCH a | THIRD SWITCH b | THIRD SWITCH c | SECOND SWITCH | KEY SWITCH (OPERATION FROM MODE SELECTOR 51) | COMMERCIAL AC POWER SOURCE AND PLUG |
|---|---|---|---|---|---|---|
| EXCLUSIVE CHARGING MODE | OFF | OFF | OFF | OFF | OFF | CONNECTION |
| CHARGING AND AC DRIVING MODE | ON/OFF | ON/OFF | ON/OFF | OFF | ON | CONNECTION |
| BATTERY DRIVING MODE (ALL FUNCTIONS) | ON | ON | ON | ON | ON | NON-CONNECTION |
| BATTERY DRIVING MODE (IMAGING CONTROL) | OFF | OFF | OFF | ON | ON | NON-CONNECTION |
| BATTERY DRIVING MODE (UNIT) | ON/OFF | ON/OFF | ON/OFF | OFF | ON | NON-CONNECTION |
| STOP MODE | OFF | OFF | OFF | OFF | OFF | NON-CONNECTION | ns
MOBILE X-RAY APPARATUS

TECHNICAL FIELD

The present invention relates to a mobile X-ray apparatus, and more particularly, to a charging technique.

BACKGROUND ART

PTL 1 discloses a mobile X-ray imaging apparatus that is capable of confirming imaging content or performing image processing during charging of a battery, in which switching is performed between commercial AC power source driving and battery driving after a predetermined time lag elapses, in order to cope with intermittent connection of a power source plug when the power source plug is connected and disconnected.

CITATION LIST

Patent Literature

[PTL 1] JP-A-2010-94327

SUMMARY OF INVENTION

Technical Problem

In general, a sudden voltage drop or momentary power interruption may occur in a commercial AC power source. In the mobile X-ray apparatus disclosed in PTL 1, if the voltage drop or momentary power interruption occurs when imaging content is confirmed or image processing is performed by an operation of the commercial AC power source, a voltage to be supplied to a unit (an image reading device that reads a latent image accumulated in an imaging plate, a controller that performs control for input setting of imaging conditions or display of an image read in the image reading device, or the like) installed in the mobile X-ray apparatus falls to or below a regulated value, and thus, a problem arises that its operation is unstable.

An object of the present invention is to provide a mobile X-ray apparatus that is capable of performing a stable operation in which a voltage to be supplied to a unit does not fall to or below a regulated value even in a case where a sudden voltage drop or momentary power interruption occurs during operation of a commercial AC power source.

Solution to Problem

In order to solve the problem, according to an aspect of the invention, there is provided a mobile X-ray apparatus which includes an external power source connector for connection to an external power source, a battery charged by the external power source through the external power source connector, and a unit that operates by being supplied with electricity using the external power source through the external power source connector, including: a first circuit that is installed between the external power source connector and the unit and includes a first rectifier; and a second circuit that is installed between the battery and the unit and includes a second rectifier, in which in a case where a voltage supplied from the external power source to the unit through the first circuit is lower than an output voltage of the battery, electricity is supplied to the unit from the battery through the second circuit.

Advantageous Effects of Invention

According to the invention, it is possible to perform a stable operation in which a voltage to be supplied to a unit does not fall to or below a regulated value even in case where a sudden voltage drop or momentary power interruption occurs during operation of an external power source (commercial AC power source). Further, it is possible to use the unit during charging, and thus, it is possible to perform imaging preparation or an image reading operation regardless of the remaining capacity of a battery.

BRIEF DESCRIPTION OF DRAWINGS

FIG. 3 is a diagram illustrating a correspondence relationship between each mode of the mobile X-ray apparatus according to the first embodiment, ON/OFF of a first switch 26, a second switch 41 and a key switch (operation through a mode selector 51), and connection/non-connection of a commercial power source (plug).

FIG. 4 is a block diagram illustrating an internal configuration in a charging and AC driving mode of the mobile X-ray apparatus according to the first embodiment.

FIG. 7 is a diagram illustrating a correspondence relationship between each mode of the mobile X-ray apparatus according to the second embodiment, ON/OFF of a second switch 41, a third switch a61, a third switch b62, a third switch c63 and a key switch (operation through a mode selector 51), and connection/non-connection of a commercial power source (plug).

DESCRIPTION OF EMBODIMENTS

Figure 1:
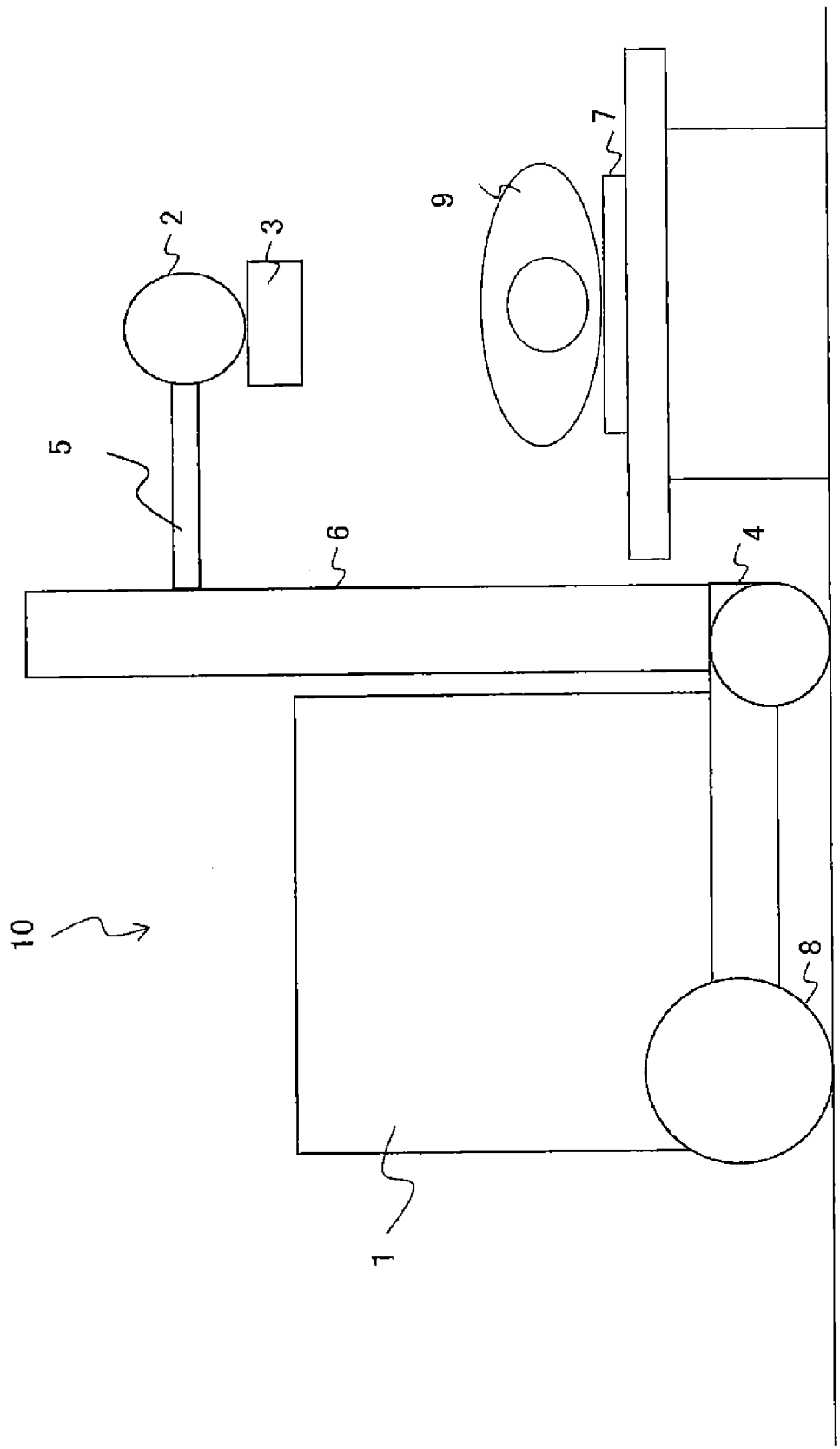
FIG. 1 is a diagram schematically illustrating an overall configuration of a mobile X-ray apparatus according to an embodiment of the invention.

Embodiments of the present invention will be described.

In order to perform a stable operation in which a voltage to be supplied to a unit does not fall to or below a regulated value even in case where a sudden voltage drop or momentary power interruption occurs during operation of a commercial AC power source, a mobile X-ray apparatus of the invention includes an external power source connector for connection to an external power source, a battery charged by the external power source through the external power source connector, and a unit that operates by being supplied with electricity using the external power source through the external power source connector, and includes a first circuit that is installed between the external power source connector and the unit and includes a first rectifier, and a second circuit that is installed between the battery and the unit and includes a second rectifier, wherein in a case where a voltage supplied from the external power source to the unit through the first circuit is lower than an output voltage of the battery, electricity is supplied to the unit from the battery through the second circuit.

Further, an end of the first circuit is connected between the external power source connector and the battery, and the other end of the first circuit is connected to the unit.

Further, the external power source is a commercial AC power source, and a voltage convertor that converts an AC voltage output from the commercial AC power source into a predetermined AC voltage is connected to the external power source connector, an AC-DC converter that converts an alternating current output from the voltage converter into a direct current is connected to the voltage converter, a battery charger that charges the battery using the direct current output from the AC-DC converter is connected to the AC-DC converter, and the battery is connected to the battery charger, and wherein the one end of the first circuit is connected to an output side of the AC-DC converter, and the other end of the first circuit is connected to the unit.

Further, the first rectifier is a first diode, the second rectifier is a second diode, an anode side of the first diode is connected to the output side of the AC-DC converter, a cathode side of the first diode is connected to the unit, an anode side of the second diode is connected to the side of the battery, and a cathode side of the second diode is connected to the cathode side of the first diode.

Further, the unit includes at least one unit section that realizes a predetermined function, and the mobile X-ray apparatus includes selection means configured to select the unit section driven by at least one of the external power source and the battery.

Further, the unit section includes a unit voltage converter that performs conversion into a voltage according to the unit section.

Further, the unit section is at least one of an image reading device that reads an image signal from an imaging plate, an operation unit that performs input setting of an imaging condition, and communication means capable of being connected to an external network.

Further, the mobile X-ray apparatus further includes stopping means configured to stop the electricity supply to the unit using the external power source when the battery is charged using the external power source, wherein the stopping means includes a switch provided between a contact point of the cathode side of the first diode and the cathode side of the second diode and the unit.

According to the invention, it is possible to provide a mobile X-ray apparatus that is capable of performing a stable operation in which a voltage to be supplied to a unit does not fall to or below a regulated value even in case where a sudden voltage drop or momentary power interruption occurs during operation of an external power source (commercial AC power source).

Hereinafter, embodiments of the invention will be described in detail with reference to the drawings. Elements having the same function are given the same reference numeral, and description thereof will not be repeated.

<Overall Configuration>

First, an overall configuration of a mobile X-ray apparatus according to an embodiment of the invention will be described with reference to FIG. 1. FIG. 1 is a diagram schematically illustrating the overall configuration of the mobile X-ray apparatus according to the present embodiment.

As shown in FIG. 1, a mobile X-ray apparatus 10 according to the present embodiment includes a main body section 1, and a carriage 4 that is mounted with the main body section 1 for movement. The main body section 1 is fixed onto the carriage 4. Further, a wheel 8 that is driven by a motor is provided in a lower part of the carriage 4. Further, a support 6 is rotatably installed in a standing manner in a front part of the carriage 4. An arm 5 that ascends and descends along the support 6 is provided to the support 6. At the tip end of the arm 5, an X-ray generator 2 that generates X-rays under the control of the main body section 1, and an X-ray movable aperture 3 that adjusts an irradiation field of X-rays are provided.

The main body section 1 includes the X-ray generator 2 and an operation panel (not shown). The X-ray movable aperture 3 is rotatably installed directly under the X-ray generator 2 and is slidably supported to the support 6 through the arm 5 together with the X-ray generator 2. The X-ray generator 2 and the X-ray movable aperture 3 move to a predetermined position according to rotation of the support 6, ascending and descending along the support 6 and extension and contraction of the arm 5 in radiography.

An X-ray detector 7 is installed to face the X-ray generator 2 in radiography, and detects X-rays that penetrate an object 9. The X-ray detector 7 includes an imaging plate that accumulates a signal of the penetrated X-rays as a latent image, an FPD (Flat Panel Detector) in which a plurality of detection elements are arranged in a two-dimensional array, and a film.

First Embodiment

Figure 2:
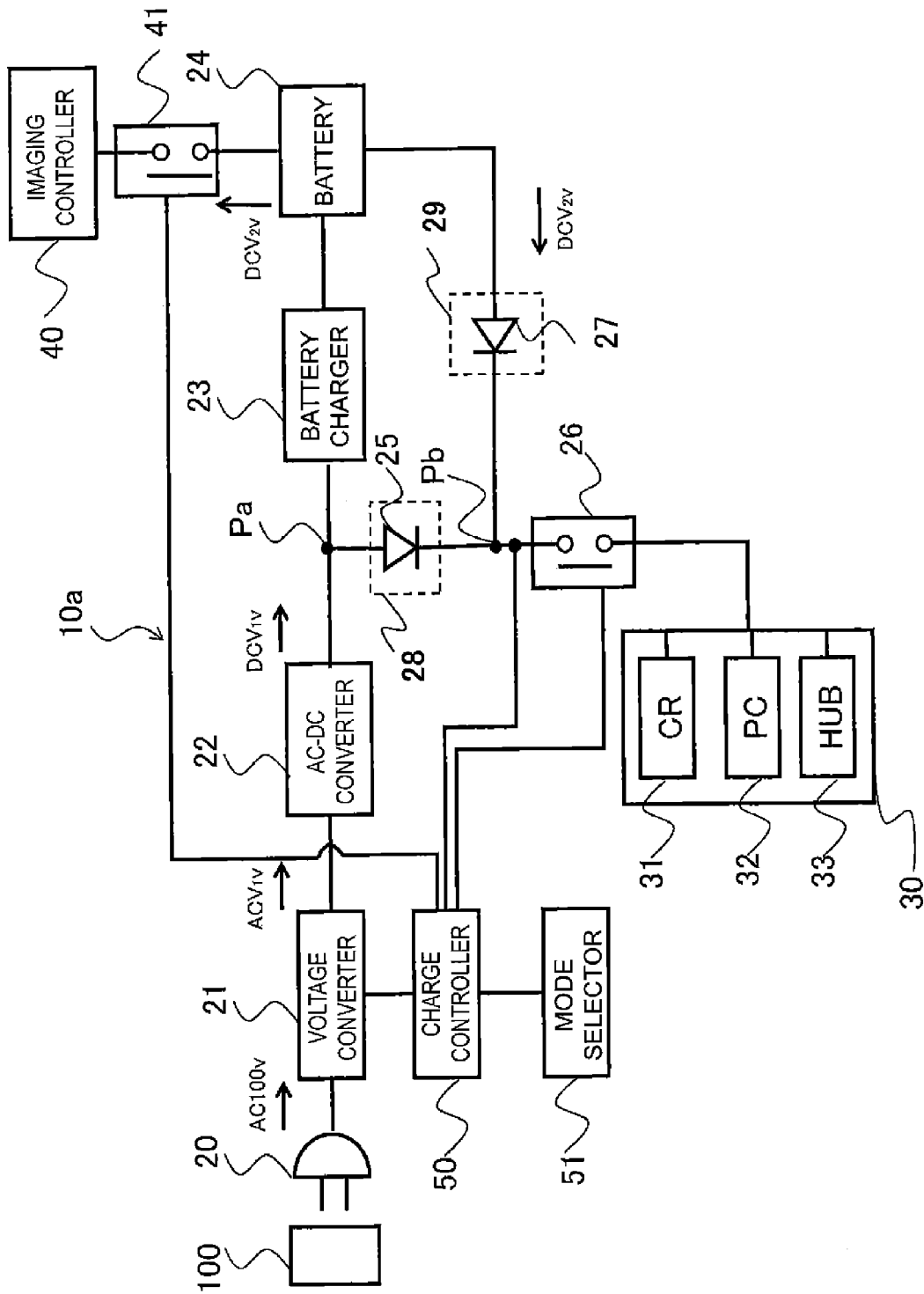
FIG. 2 is a block diagram illustrating an internal configuration of a mobile X-ray apparatus according to a first embodiment.

Next, an internal configuration of a mobile X-ray apparatus according to a first embodiment will be described with reference to FIG. 2. FIG. 2 is a block diagram illustrating the internal configuration of the mobile X-ray apparatus according to the first embodiment.

A mobile X-ray apparatus 10a according to the first embodiment includes a plug 20 that is an external power source connector for connection with a commercial AC power source 100 that is an external power source, a voltage converter 21 that converts an AC voltage output from the commercial AC power source 100 into a predetermined AC voltage, an AC-DC converter 22 that converts an alternating current output from the voltage converter 21 into a direct current, and a battery charger 23 that charges a battery 24 using the direct current output from the AC-DC converter 22. The plug 20, the voltage converter 21, the AC-DC converter 22, the battery charger 23, and the battery 24 are electrically connected to each other. A contact point Pa is provided between the AC-DC converter 22 and the battery charger 23.

The contact point Pa and a unit 30 mounted to the main body section 1 are electrically connected to each other through a first rectifier 25 and a first switch 26. In the first embodiment, the first rectifier 25 is referred to as a first circuit 28. A part of the AC converted in the AC-DC converter 22 is supplied to the unit 30 through the first circuit 28 and the first switch 26. Thus, the unit 30 is driven by the commercial AC power source 100.

In the present embodiment, unit 30 includes as unit sections: an image reading apparatus (hereinafter, simply referred to as "CR") 31 that reads the latent image accumulated in the imaging plate; a controller (hereinafter, simply referred to as "PC") 32 that performs an imaging condition input setting or a control for displaying the image read in the CR 31; and a HUB 33 that is a part of an apparatus that is connected to an external network such as a hospital LAN for communication with the external network to obtain information necessary for imaging, for example, order information indicating imaging conditions of an object are provided. These unit sections are only examples, and the unit sections included in the unit 30 are not limited. Each unit section (CR 31, the PC 32 and the HUB 33) includes therein a unit section voltage converter (not shown in the drawings) for conversion into a voltage corresponding to each unit section. In a case where the unit section is operated by a direct current, the unit section voltage converter is a DC-DC converter, but in a case where the unit section is operated by an alternating current, the unit section voltage converter is a DC-AC converter. In a case where the FPD is used as the X-ray detector 7, an image processing apparatus that generates an X-ray image of an object on the basis of an electric signal from the FPD instead of the CR 31 may be used.

The battery 24 is electrically connected to an imaging controller 40 that controls the operations of the X-ray generator 2 and the X-ray movable aperture 3, through a second switch 41. Further, the battery 24 is electrically connected to a contact point Pb between the first circuit 28 and the first switch 26 through a second rectifier 27. In the present embodiment, the second rectifier 27 is referred to as a second circuit 29.

The mobile X-ray apparatus 10 according to the present embodiment mainly includes four modes of an exclusive charging mode in which only charging is performed, a charging and AC driving mode in which the unit 30 is driven using the commercial AC power source 100 (hereinafter, referred to as "AC driving") during charging, a battery driving mode in which only battery driving is performed, and a stop mode. Further, the battery driving mode may be specifically divided into a mode in which all functions are operated, a mode in which only the imaging controller 40 is operated, and a mode in which only the unit of the main body section 1 is operated. In the present embodiment, the description will be made under the assumption that the battery driving mode is divided into the above-described three modes.

The mobile X-ray apparatus 10a includes a mode selector 51 that selects each mode using a dial type switch, a touch panel, a command switch (key switch) or the like that is provided in the main body section 1, and a charge controller 50 that transmits signals for ON/OFF of the first switch 26 and the second switch 41 according to the selected mode and performs control for a connection state corresponding to the mode. The charge controller 50 is connected to the voltage converter 21, the first switch 26, the second switch 41 and the mode selector 51, and is connected between the contact point Pb and the first switch 26. The charge controller 50 controls the ON/OFF of the first switch 26 and the second switch 41 according to the mode selected by the mode selector 51.

Figure 5:
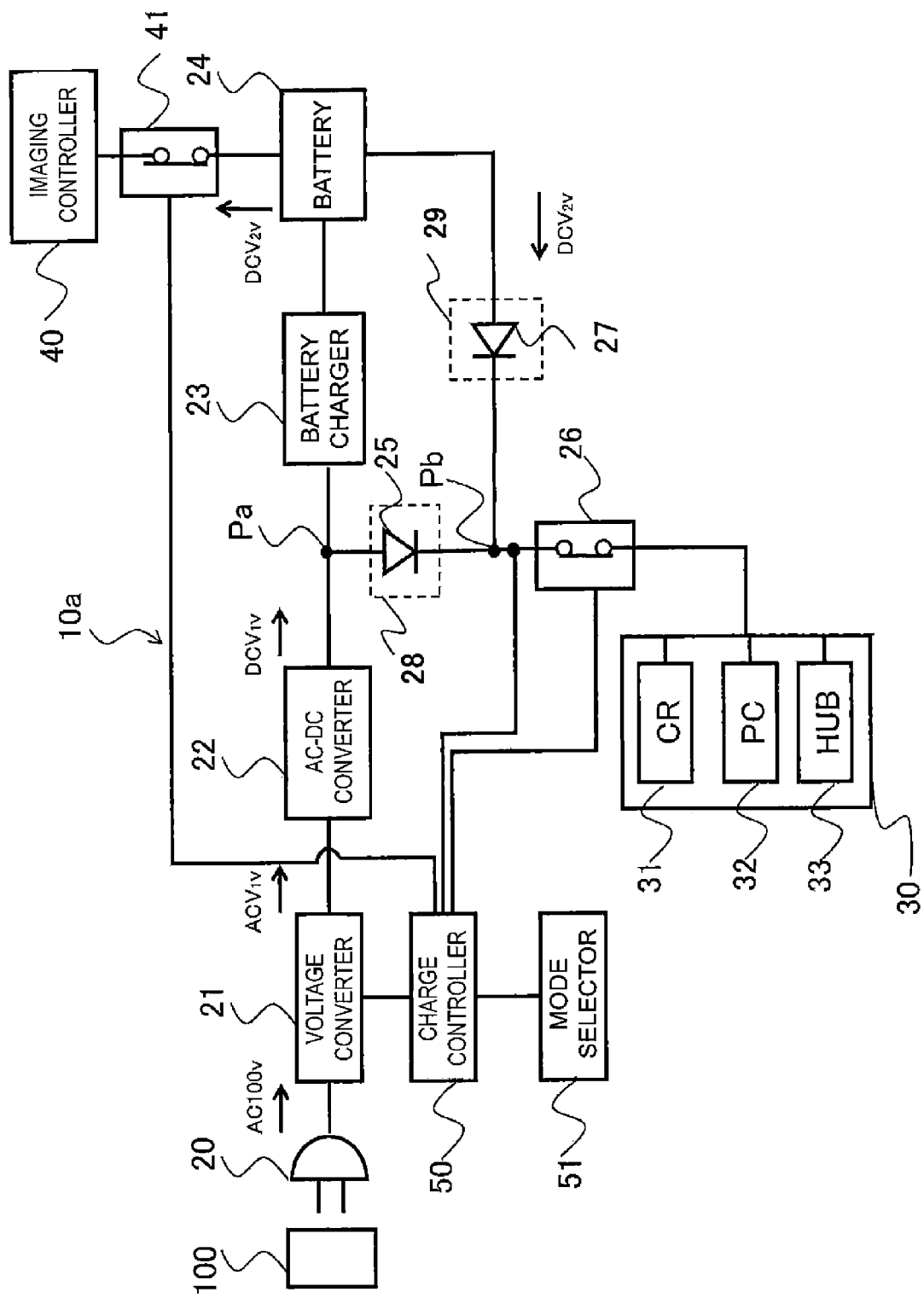
FIG. 5 is a block diagram illustrating an internal configuration in a battery driving mode (all functions) of the mobile X-ray apparatus according to the first embodiment.

Hereinafter, the respective modes will be described with reference to FIGS. 3 to 5. FIG. 3 is a diagram illustrating a correspondence relationship between each mode of the mobile X-ray apparatus 10a according to the first embodiment, ON/OFF of the first switch 26, the second switch 41 and the key switch (operation through the mode selector 51), and connection/non-connection of the commercial AC power source 100 and the plug 20. FIG. 4 is a block diagram illustrating an internal configuration in the charging and AC driving mode of the mobile X-ray apparatus 10a according to the first embodiment. FIG. 5 is a block diagram illustrating an internal configuration in the battery driving mode (all functions) of the mobile X-ray apparatus 10a according to the first embodiment.

(Exclusive charging mode)

If the key switch (operation through the mode selector 51) is turned off and the plug 20 is connected to the commercial AC power source 100, as shown in the "exclusive charge mode" in FIG. 3, the mode becomes the exclusive charge mode, and both of the first switch 26 and the second switch 41 are turned off (in FIG. 2, both of the first switch 26 and the second switch 41 are turned off, and if the plug 20 is connected in this state, the mode transits to the exclusive charge mode). As the first switch 26 is turned off, power supply from the commercial AC power source 100 to the unit 30 is stopped. In the exclusive charge mode, an AC voltage (for example, AC 100v) is supplied from the commercial AC power source 100, and is converted into ACV1v (for example, increases to AC 200v) in the voltage converter 21. Then, in the AC-DC converter 22, ACV1v is AC-DC converted into DCV1v (for example, DC 282v). Further, the DC voltage of DCV1v is supplied to the battery charger 23, and charging into the battery 24 is started. In the exclusive charge mode, since the entire DC output from the AC-DC converter 22 is used for charging, it is possible to reduce time necessary for charging.

(Charging and AC Driving Mode)

If the key switch is turned on in a state where the plug 20 is connected to the commercial AC power source 100, the mode becomes the charging and AC driving mode, and as shown in FIG. 4, the first switch 26 is turned on and the second switch 41 is turned off (see the "charging and AC driving mode" in FIG. 3). In the charging and AC driving mode, an AC voltage (for example, AC 100v) is supplied from the commercial AC power source 100, and is converted into $ACV_1v$ in the voltage converter 21. Then, in the AC-DC converter 22, $ACV_1v$ is AC-DC converted into $DCV_1v$ (for example, DC 282v). A part of the DC output from the AC-DC converter 22 is transmitted to the battery charger 23, and charging into the battery 24 is started. At the same time, the remaining DC output from the AC-DC converter 22 is transmitted to the first circuit 28. Accordingly, $DCV_1v$ is applied to the first circuit 28. $DCV_1v$ is applied to the unit 30 through the first switch 26.

On the other hand, since a DC voltage of $DCV_2v$ (for example, DC 200v) that is lower than $DCV_1v$ is supplied from the battery 24, $DCV_2v$ is applied to the second circuit 29.

While the electric current is being stably supplied from the commercial AC power source 100, the unit 30 is supplied with the DC voltage of $DCV_1v$ through the first circuit 28 and the first switch 26, and the unit 30 is driven by the commercial AC power source 100.

If the supply of the electric current from the commercial AC power source 100 becomes unstable and momentary power interruption including a voltage drop occurs, and as a result, the output from the AC-DC converter 22 is stopped or becomes lower than $DCV_2v$, the DC voltage of $DCV_2v$ is supplied to the unit 30 from the battery 24 through the contact point Pb in a moment. That is, if the voltage from the commercial AC power source 100 is equal to or lower than a regulated value (voltage $DCV_2v$ output from the battery 24) while the unit 30 is being driven by the electricity supply from the commercial AC power source 100 that is the external power source, electricity is supplied to the unit 30 from the battery 24. In other words, according to an electric potential difference between the voltage output from the AC-DC converter 22 and the voltage output from the battery 24, electricity is supplied to the unit 30 from one having a higher electric potential among the AC-DC converter 22 and the battery 24.

If the voltage supplied from the AC-DC converter 22 is equal to or lower than a predetermined value (for example, $DCV_2v$), the charging performance deteriorates, and thus, a configuration in which charging into the battery 24 is stopped and the entire electric power is used for supply to the unit 30 may be used.

(Battery Driving Mode)

At the time of round, the mobile X-ray apparatus 10a is moved to a bed side of the object 9, various operations such as X-ray irradiation and image reading are performed by driving of the battery 24. Thus, in the battery driving mode, a mode in which all functions are operated is selected in many cases. Accordingly, first, in the battery driving mode, the mode in which all functions are operated will be described. In a state where the plug 20 is not connected to the commercial AC power source 100, if an input operation of turning on the key switch is performed, the mode becomes the battery driving mode (all functions), and as shown in FIG. 5, both the first switch 26 and the second switch 41 are turned on (see the "battery driving mode (all functions)" in FIG. 3). In this state, the X-ray generator 2 and the X-ray detector 7 face each other with the object 9 being interposed therebetween, and a DC voltage (DCV2v) is applied to the imaging controller 40 from the battery 24 to irradiate the X-rays. Further, DCV2v is applied to the unit 30 from the battery 24, the CR 31 and the PC 32 are operated, and the HUB 33 is operated as necessary. Then, image reading or display and order information reception are performed.

In the battery driving mode, in principle, it is possible to use all functions of the mobile X-ray apparatus 10a, but by adding a function of limiting and selecting the function of driving the battery 24 by the mode selector 51, for example, a selection function of respective modes such as "a battery driving mode (all functions)", "a battery driving mode (imaging control)" and "a battery driving mode (unit)" in addition to ON/OFF of the key switch, it is possible to select the "battery driving mode (imaging control)" in which only the radiography is performed and the "battery driving mode (unit)" in which only the unit 30 of the main body unit 1 is operated, for example. That is, if the key switch of the "battery driving mode (imaging control)" is turned on in a state where the plug 20 is not connected to the commercial AC power source 100, the charge controller 50 turns off the first switch 26, and turns on the second switch 41. Similarly, if the key switch of the "battery driving mode (unit)" is turned on in a state where the plug 20 is not connected to the commercial AC power source 100, the charge controller 50 turns on the first switch 26, and turns off the second switch 41 (see the "battery driving mode (imaging control)" and the "battery driving mode (unit)" in FIG. 3).

(Stop Mode)

If the key switch is turned off in a state where the plug 20 is not connected to the commercial AC power source 100, the charge controller 50 turns off both the first switch 26 and the second switch 41, and the electric power is completely cut off.

According to the present embodiment, while the plug 20 is being connected to the commercial AC power source 100 to charge the battery 24, it is possible to operate the respective functions of the unit 30.

Normally, after the mobile X-ray apparatus 10a is moved to a location where the mobile X-ray apparatus 10a is to be kept after round, charging of the mobile X-ray apparatus 10a is performed for preparation of the next round, or is performed in a case where the remaining capacity of the battery 24 is insufficient in preparation before round, in many cases. During charging, for example, it is possible to obtain order information about the object 9 through the HUB 33, to perform input setting of imaging condition from an operation unit by driving the PC 32, or to perform image reading by driving the CR 31, and thus, it is possible to perform imaging preparation or an image reading operation even during charging.

Further, even in a case where a voltage drop of the commercial AC power source 100 or momentary power interruption occurs during charging, a direct current is supplied in a moment from the battery 24 through the second circuit 29, and thus, it is possible to stably operate the operation of the unit 30 without forced termination. Thus, regardless of the power source supply situation of the commercial AC power source 100, it is possible to perform a stable operation of the unit 30 and suppress occurrence of malfunction associated with sudden operation termination of the unit 30.

Further, in the present embodiment, the first switch 26 is used, but it is also possible to show the effect of achieving the stable operation by connecting the contact point Pb to the unit 30 directly, without using the first switch 26. Here, in this case, the setting of the exclusive charge mode, the battery driving mode (imaging control) and the stop mode are not performed.

Second Embodiment

Figure 6:
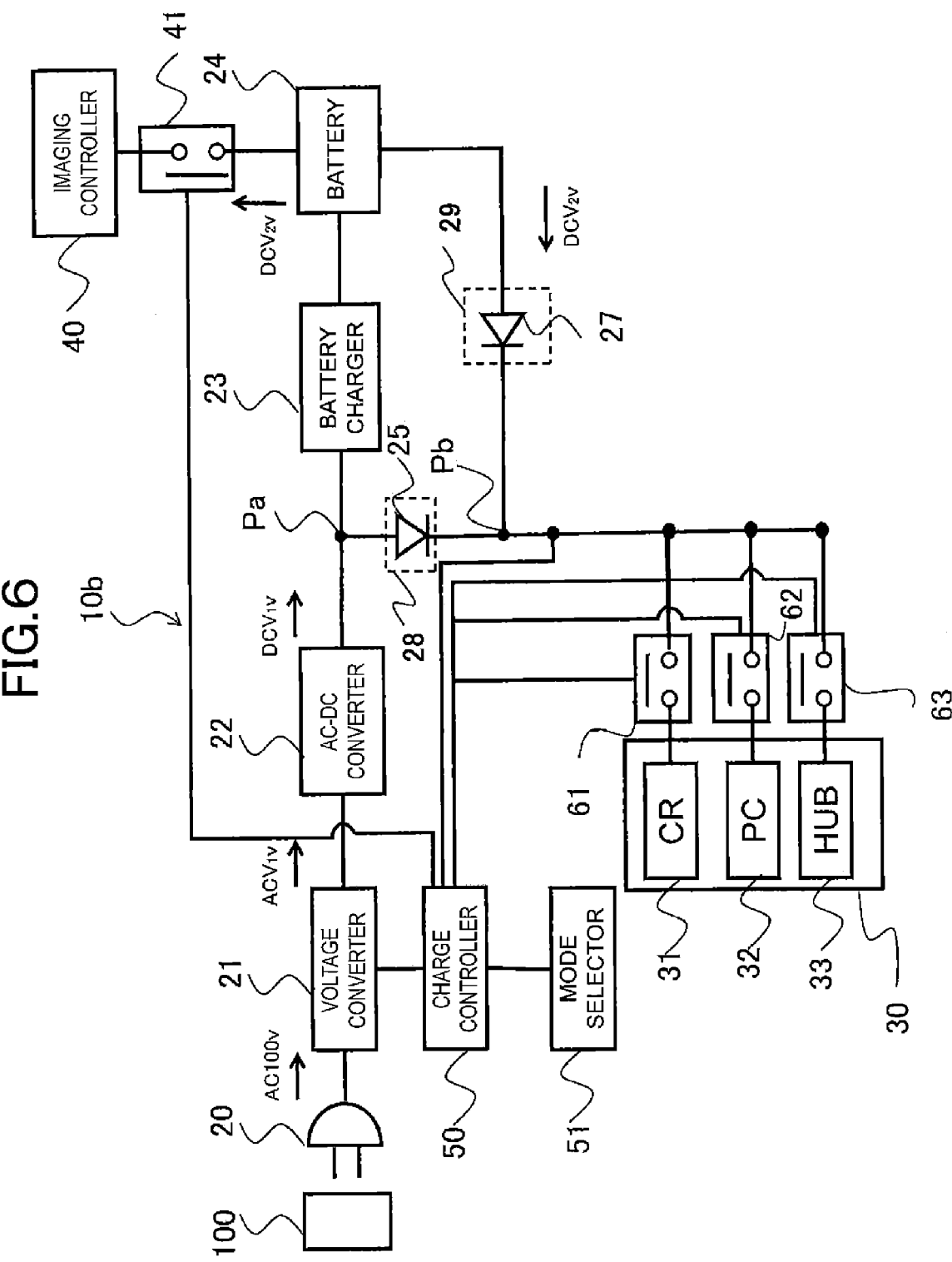
FIG. 6 is a block diagram illustrating an internal configuration of a mobile X-ray apparatus according to a second embodiment.

Another embodiment will be described with reference to FIGS. 6 and 7. FIG. 6 is a block diagram illustrating an internal configuration of a mobile X-ray apparatus 10b according to a second embodiment. FIG. 7 is a diagram illustrating a correspondence relationship between each mode of the mobile X-ray apparatus 10b according to the second embodiment, ON/OFF of the second switch 41, a third switch a 61, a third switch b 62, and a third switch c 63 and a key switch (operation through the mode selector 51), and connection/non-connection of a commercial power source (plug).

A mobile X-ray apparatus 10b according to the second embodiment is different from the mobile X-ray apparatus 10a according to the first embodiment in that whether or not driving is to be performed is selected in the unit of the unit 30 in the first embodiment, whereas selection and driving are performed in the unit of functions in the unit 30 in the second embodiment. That is, the selection and driving are performed for each of the CR 31, the PC 32 and the HUB 33 that are unit sections that realize predetermined functions.

As shown in FIG. 6, the mobile X-ray apparatus 10b according to the second embodiment includes the third switch a 61, the third switch b 62, and the third switch c 63 as selection means configured to select unit sections, which respectively turn on or off the CR 31, the PC 32 and the HUB 33 that are the unit sections of the unit 30, instead of the first switch 26 of the mobile X-ray apparatus 10a according to the first embodiment. Further, as the mode selector 51 selects the charging and AC driving mode or the battery driving mode and selects a function to be driven, it is possible to AC-drive only a desired function during charging.

That is, in the present embodiment, it is possible to select ON/OFF for each of the CR 31, the PC 32 and the HUB 33 that are the unit sections that realize the functions of the unit 30, compared with the first embodiment in which the selection of ON/OFF is performed in the unit 30 of the unit 30. Here, in the battery driving (all functions) mode, since all functions are operated, the third switch a 61, the third switch h 62, and the third switch c 63 are all turned on.

Further, since the "battery driving (imaging control) mode" of the present embodiment is defined as a mode in which only the imaging controller 20 is operated, the third switch a 61, the third switch b 62, and the third switch c 63 are turned off in FIG. 7, but a configuration may be used in which a function to be operated together with the imaging controller 20 is selected for operation.

In this case, the third switch a 61, the third switch b 62, and the third switch c 63 in the "battery driving (imaging control) mode" in FIG. 7 may be rewritten as "ON/OFF". Thus, it is possible to select only a desired function of the unit 30 for operation together with the imaging controller 40.

According to the present embodiment, since it is possible to select whether the operation is performed for each of the unit sections that realize the functions of the unit 30, it is possible to reduce the charging time in the charging and AC driving mode and to achieve power saving in the operation of the battery driving mode.

Further, as the selection means is provided, it is possible to select the unit sections to be driven by at least one of the commercial AC power source 100 and the battery 24.

Any modification in a range without departing from the spirit of the invention belongs to the technical scope of the invention. Accordingly, for example, the number, position or the like of each component such as a switch or a voltage converter is not limited to the above-described embodiments.

REFERENCE SIGNS LIST

1 MAIN BODY SECTION
2 X-RAY GENERATOR
3 X-RAY MOVABLE APERTURE
4 CARRIAGE
5 ARM
6 SUPPORT
7 X-RAY DETECTOR
9 OBJECT
10 MOBILE X-RAY APPARATUS

The invention claimed is:

1. A mobile X-ray apparatus comprising:
   an external power source connector for connection to an external power sources;
   a battery charged by the external power source through the external power source connector;
   a unit that operates by being supplied with electricity using the external power source through the external power source connector;
   a first circuit that is installed between the external power source connector and the unit and includes a first rectifier; and
   a second circuit that is installed between the battery and the unit and includes a second rectifier,
   wherein in a case where a voltage supplied from the external power source to the unit through the first circuit is lower than an output voltage of the battery, electricity is supplied to the unit from the battery through the second circuit.

2. The mobile X-ray apparatus according to claim 1,
   wherein an end of the first circuit is connected between the external power source connector and the battery, and the other end of the first circuit is connected to the unit.

3. The mobile X-ray apparatus according to claim 2, wherein the external power source is a commercial AC power source, further comprising;
   a voltage convertor connected to the external power source connector that converts an AC voltage output from the commercial AC power source into a predetermined AC voltage;
   an AC-DC converter connected to the voltage converter that converts an alternating current output from the voltage converter into a direct current; and
   a battery charger connected to the AC-DC converter and the battery that charges the battery using the direct current output from the AC-DC converter,
   wherein the end of the first circuit is connected to an output side of the AC-DC converter, and the other end of the first circuit is connected to the unit.

4. The mobile X-ray apparatus according to claim 3,
   wherein the first rectifier is a first diode, the second rectifier is a second diode, an anode side of the first diode is connected to the output side of the AC-DC converter, a cathode side of the first diode is connected to the unit, an anode side of the second diode is connected to the battery, and a cathode side of the second diode is connected to the cathode side of the first diode.

5. The mobile X-ray apparatus according to claim 4, further comprising:
   stopping means configured to stop the electricity supply to the unit using the external power source when the battery is charged using the external power source,
   wherein the stopping means includes a switch provided between a contact point of the cathode side of the first diode and the cathode side of the second diode and the unit.

6. The mobile X-ray apparatus according to claim 1,
   wherein the unit includes at least one unit section that realizes a predetermined function, and the mobile X-ray apparatus includes selection means configured to select a unit section of the at least one unit section driven by at least one of the external power source and the battery.

7. The mobile X-ray apparatus according to claim 6,
   wherein the at least one unit section includes a unit voltage converter that performs conversion into a voltage according to the at least one unit section.

8. The mobile X-ray apparatus according to claim 6,
   wherein the at least one unit section is at least one of an image reading device that reads an image signal from an imaging plate, an operation unit that performs input setting of an imaging condition, and communication means capable of being connected to an external network.

* * * * *